United States Patent [19]
Ishiguro et al.

[11] Patent Number: 6,063,572
[45] Date of Patent: May 16, 2000

[54] METHOD OF ASSAY OF NUCLEIC ACID SEQUENCES

[75] Inventors: Takahiko Ishiguro, Yokohama; Juichi Saitoh, Yamato, both of Japan

[73] Assignee: Tosoh Corporation, Shinnanyo, Japan

[21] Appl. No.: 09/012,573

[22] Filed: Jan. 23, 1998

[30] Foreign Application Priority Data

Jan. 24, 1997 [JP] Japan ................................. 9-010996

[51] Int. Cl.[7] ............................................ C12Q 1/68
[52] U.S. Cl. ....................... 435/6; 435/91.1; 435/91.2; 935/77; 935/78
[58] Field of Search .................. 435/6, 91.2; 935/77, 935/78

[56] References Cited

U.S. PATENT DOCUMENTS 5,814,447  9/1998  Ishiguro et al. ............................. 435/6

FOREIGN PATENT DOCUMENTS

| | | |
|---|---|---|
| 0 310 229 | 4/1989 | European Pat. Off. . |
| 0 487 218 | 5/1992 | European Pat. Off. . |
| 0 714 986 | 6/1996 | European Pat. Off. . |

OTHER PUBLICATIONS

Takahiko Ishiguro, et al., Nucleic Acids Research, vol. 24, No. 24, pp. 4992–4997, "Fluorescence Detection of Specific Sequence of Nucleic Acids by Oxazole Yellow–Linked Oligonucleotides. Homogeneous Quantitative Monitoring of in vitro Transcription", 1996.

Takahiko Ishiguro, et al., Analytical Biochemistry, vol. 229, No. 2, pp. 207–213, "Homogeneous Quantitative Assay of Hepatitis C Virus RNA by Polymerase Chain Reaction in the Presence of Fluorescent Intercalater", Aug. 10, 1995.

*Primary Examiner*—Kenneth R. Horlick
*Assistant Examiner*—Janell Taylor
*Attorney, Agent, or Firm*—Oblon, Spivak, McClelland, Maier & Neustadt, P.C.

[57] ABSTRACT

A method of assay of a specific nucleic acid anticipated in a sample, which comprises:

a DNA producing step which involves production of a double-stranded DNA having a promoter sequence for an RNA polymerase and the nucleic sequence of the specific nucleic acid (the specific nucleic acid sequence) downstream from the promoter sequence by using the specific nucleic acid in the sample as a template, and an RNA producing and measuring step which involves production of a single-stranded RNA having the specific nucleic acid sequence by the RNA polymerase and measurement of the single-stranded RNA, wherein the RNA producing and measuring step is initiated by adding at least the RNA polymerase, ribonucleoside triphosphates and a probe which is labeled with a fluorescent intercalative dye and is complementary to the single-stranded RNA to the reaction solution after the DNA producing step, involves measurement of the fluorescence intensity of the reaction solution, and is carried out at a constant temperature, and does not involve denaturing and annealing procedure for hybridization or separation of the probe which has not hybridized with the single-stranded RNA produced.

21 Claims, 4 Drawing Sheets

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:Synthetic DNA

<400> SEQUENCE: 1
actcgcaagc accctatc                                                      18

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence:Synthetic DNA

<400> SEQUENCE: 2
atttaggtga cactatagaa tacaacactc caccatagat cactc                        45

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:Synthetic DNA

<400> SEQUENCE: 3
ctcgcggggg ctg                                                           13

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthetic DNA

<400> SEQUENCE: 4
gcactcgcaa gcaccctatc a                                                  21

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence:Synthetic DNA

<400> SEQUENCE: 5
atttaggtga cactatagaa tacaacactc caccatagat cactcccctg                   50

METHOD OF ASSAY OF NUCLEIC ACID SEQUENCES

The present invention relates to a method of detection or quantification of a specific nucleic acid anticipated in a gene mixture containing DNA or RNA, and is useful for gene diagnosis in the field of clinical diagnosis, for cloning useful genes and for exploring unknown genes. The present invention is also useful as a method of optimizing the reaction conditions for amplification of genes.

The assay of a specific nucleic acid by using a probe (a nucleic acid probe) which is complementary in base sequence to the nucleic acid utilizes the ability of the specific nucleic acid to hybridize with the probe.

For example, a method called the sandwich assay has been known which uses two probes which hybridize with different parts of the specific nucleic acid. In this method, one of the probes is immobilized on a solid support, while the other is labeled with a dye which is visible by its color or a fluorescent substance or an enzyme which catalyzes production of such a dye or a fluorescent substance. These probes are added to a sample and allowed to hybridize with the specific nucleic acid in the sample so that a complex of the three is formed on the solid support. Then, the solid support is separated from the supernatant of the sample solution to separate the unhybridized second probe (B/F separation step). Subsequently, the label in the complex on the solid support is measured to detect and quantify the specific nucleic acid and in the sample. When an enzyme which catalyzes production of a dye which is visible by its color or a fluorescent substance is used to label the second probe, after the formation of the complex, the unhybridized second probe is removed, and a substrate of the enzyme as the precursor of the dye or the fluorescent substance, is added to the sample solution. The dye or the fluorescent substance as the reaction product is measured to detect and quantify the nucleic acid in the sample.

In recent years, by virtue of the development of the polymerase chain reaction, it has become possible to amplify a specific region of a specific nucleic acid in a sample, to an amount that is enough to assay. The detection and quantification of a specific nucleic acid in a sample is carried out by amplifying a specific region of the specific nucleic acid by PCR and then measuring the amplification product in the PCR reaction mixture by the sandwich assay as mentioned above. It is also proposed to amplify a specific region of a specific nucleic acid sequence by PCR as described above, add probes complementary to the specific region to the reaction solution under such conditions which allow the probes to hybridize with the amplified nucleic acid, electrophoretically separate the resulting complex from the unhybridized probes and then measure the amplification product.

Because the sandwich assay uses a solid support in the reaction mixture, the second probe is non-specifically adsorbed on the solid support, and the presence of the label of the second probe non-specifically adsorbed on the solid support produces errors in the measurement of the labeled hybrid on the solid support, which causes problems in detection and quantification of a specific nucleic. Especially, because diagnosis of virus infections requires sensitive detection of trace amounts of virus nucleic acids in clinical samples with good reproducibility, the above-mentioned problem attributable to the non-specific adsorption is a serious problem to be solved.

With a view to obviating this problem, treatment for making the surface of a solid support hydrophilic, blocking of the adsorptive sites on a support with protein and thorough washing of a solid support after the B/F separation have been attempted.

However, chemical treatment for making the surface of a support hydrophilic but does not succeed depending on the material of the support and can be technically difficult. Also, when the surface of a support is covered with protein in order to block the adsorptive sites on the surface of the support, the interaction between the protein and the nucleic acid segment or the label of the second probe can cause another kind of non-specific adsorption. In addition, the number of repetitions of washing the solid support in the B/F separation is operationally limited, and for example, a cleaning solution containing a surfactant can induce decomposition of the hybrid formed on the support.

In the case of a sandwich assay subsequent to amplification of a specific region of a specific nucleic acid by PCR, since the product of the amplification by PCR is a double-stranded DNA, in order to hybridize the probes and the amplified nucleic acid, a heating procedure for melting the double-stranded DNA as the amplification product into single strands after addition of the probes to the PCR reaction mixture (denaturing) and a subsequent cooling procedure for formation of a double-stranded DNA from the probe DNA and the target DNA (annealing) are essential. Therefore, this assay requires additional labor and more analysis time for practical clinical diagnoses, where effectiveness and economy are two important objectives.

In the above-mentioned method utilizing electrophoresis, the necessity to sample the amplification products from the reaction vessels for the analysis after PCR can cause a problem of false positive results attributable to carryover of the amplification products, which is an obstacle to practical application of PCR.

Therefore, it is desired to develop an assay method which does not use such a support, does not involve denaturing and annealing procedures at the time of measuring the label of the probe, and minimizes carryover of the nucleic acid amplified by PCR.

A support-free assay method which comprises conducting PCR in the presence of a fluorescent intercalative dye and measuring the fluorescence intensity of the reaction solution is proposed (Japanese Unexamined Patent Publication JP-A-5-237000, Igaku-no Ayumi 173(12), 959–963 (1995), and Analytical Biochemistry, 229, 207–213(1995)). Namely, because the PCR products are double-stranded DNA, a fluorescent intercalative dye which alters the fluorescent property, for example increases the fluorescent intensity, on intercalation with a double-stranded nucleic acid, is added to a sample solution before amplification by PCR and the fluorescence intensity of the reaction solution is monitored to detect or quantify the target nucleic acid before the amplification.

This method makes it possible to follow the progress of PCR by measuring the fluorescence intensity of reaction solutions in sealed vessels, and can obviate the problem of false positive results attributable to carryover of the amplification products because it does not require sampling of reaction solutions from reaction vessels.

Thus, the above-mentioned assay by performing PCR in the presence of a fluorescent intercalative dye and monitoring the fluorescence intensity of a PCR reaction solution is excellent as a support-free, or homogeneous one-step assay.

However, because fluorescent intercalative dyes non-specifically bind double-stranded nucleic acids, when samples contain larger amounts of genomic DNA in addition to the specific nucleic acid, the assay method has a problem that intercalation of a fluorescent intercalative dye with the genomic DNA gives a high background count and thereby makes it difficult to accurately measure the change in the fluorescence intensity attributable to the amplification of the specific nucleic acid. Further, the two nucleic acids which are complementary to specific regions of a specific nucleic acid and used as the primers for the elongation reaction in PCR can bind complimentarily to each other, depending on their sequences, and in such a case, serve as a template for each other to produce a primer dimer. Because a fluorescent intercalative dye non-specifically intercalates also to the primer dimer, the increased background attributable to the non-specific intercalation is a problem in monitoring the change in the fluorescent property based on amplification of the specific nucleic acid.

In order to solve this problem, a method of assaying nucleic acids by using a fluorescent intercalative dye-labeled probe capable of recognizing a specific nucleic acid sequence which comprises a single-stranded oligonucleotide complementary in nucleic acid sequence to the specific nucleic acid sequence of the target specific nucleic acid and a fluorescent intercalative dye linked to the single-stranded oligonucleotide as a label, and is designed so that when the single-stranded oligonucleotide hybridizes with the specific nucleic acid, the intercalative dye intercalates with the resulting double-stranded oligonucleotide to alter the fluorescent property, has been developed (Japanese Patent Application JP7-185599, EP-A-714986, Nucleic Acids Research 24(24), 4992–4997(1996)). Since the fluorescent intercalative dye as the label alters fluorescent property upon hybridization of the probe with the specific nucleic acid, the method enables detection and quantification of the resulting hybrid without separating the unhybridized probe. Further, if the probe is added to the sample before the specific nucleic acid is amplified, it is possible to monitor the amplification of the nucleic acid based on the sequence specificity by measuring the fluorescence intensity of the reaction solution during the amplification.

The present inventors have conducted studies to provide a method for support-free or homogeneous assay of a specific nucleic acid by using a fluorescent intercalative dye, which is enough specific for the specific nucleic acid sequence to allow a precise assay even if the sample contain a large amount of genomic DNA or even if a primer dimer is produced during amplification by PCR prior to the assay, and which can detect or quantify the specific nucleic acid sequence at a constant temperature without separation of the excessive probe and the denaturing and annealing procedures, and as a result, have accomplished the present invention.

Namely, the present invention provides a method of assay of a specific nucleic acid anticipated in a sample, which comprises:

a DNA producing step which involves production of a double-stranded DNA having a promoter sequence for an RNA polymerase and the nucleic sequence of the specific nucleic acid (the specific nucleic acid sequence) downstream from the promoter sequence by using the specific nucleic acid in the sample as a template, and an RNA producing and measuring step which involves production of a single-stranded RNA having the specific nucleic acid sequence by the RNA polymerase and measurement of the single-stranded RNA, wherein the RNA producing and measuring step is initiated by adding at least the RNA polymerase, ribonucleoside triphosphates and a probe which is labeled with a fluorescent intercalative dye and is complementary to the single-stranded RNA to the reaction solution after the DNA producing step, involves measurement of the fluorescence intensity of the reaction solution, and is carried out at a constant temperature, and does not involve denaturing and annealing procedure for hybridization or separation of the probe which has not hybridized with the single-stranded RNA produced.

The present invention will be described in detail below.

In the DNA producing step, double-stranded DNA consisting of a promoter sequence for an RNA polymerase and a specific nucleic acid sequence following the promoter sequence is produced by using the specific nucleic acid. In the step, a pair of primers which are complementary in sequence to the specific nucleic acid sequence are used, and one of them is a promoter primer which has a promoter sequence for an RNA polymerase at the 5'-end. In the step, a DNA polymerase and deoxyribonucleoside triphosphates are also used.

Namely, the above-mentioned double-stranded DNA is produced by DNA elongation reaction by the repeated action of DNA polymerase by using the above-mentioned two primers.

The DNA polymerase used in the present invention is not particularly limited, and for example, E. coli DNA polymerase III, the Klenow flagment, T4 DNA polymerase, T7 DNA polymerase, Thermus aquaticus DNA polymerase, Thermus Thermophilus DNA polymerase and the like may be used.

The promoter primer used in the present invention is designed to have at least the promoter sequence for an RNA polymerase and a sequence complementary to the specific nucleic acid sequence in this order from the 5' end toward the 3' end, as described above. The segment which is complementary to the specific nucleic acid is complementary at least to part of the specific nucleic acid, not necessarily to the entire specific nucleic acid sequence. The segment is from 6 to 100 nucleotides long, preferably from 10 to 30 nucleotides long in order to secure the specificity for a nucleic acid complementary to the specific nucleic acid. The promoter sequence for an RNA polymerase and the sequence complementary to the specific nucleic acid sequence may be linked via a few bases (linker bases) which are related to neither of them. When the specific nucleic acid is RNA, the above-mentioned DNA elongation reaction is preceded by synthesis of cDNA by using the specific nucleic acid as a template in the DNA producing step. For the synthesis of cDNA, the above-mentioned two primers containing sequences complementary to the specific nucleic acid sequence, a reverse transcriptase and the substrates for the reverse transcriptase, deoxyribonucleoside triphosphates are used. Either of the primers used in the DNA producing step may be used for the synthesis of cDNA, and in this case, the other primer has to be added to the reaction solution for the synthesis of double-stranded DNA by a DNA polymerase subsequent to the synthesis of cDNA. The reverse transcriptase is not particularly limited, and those commercially available can be used. Further, in the case of a DNA polymerase having a reverse transcription activity, it is possible to perform the synthesis of cDNA and the synthesis of double-stranded DNA without discontinuity by adding a reagent containing the above-mentioned two primers, the DNA polymerase and deoxyribonucleoside triphosphates to a sample.

In the RNA producing and measuring step subsequent to the DNA producing step, a single-stranded RNA is synthesized by the action of an RNA polymerase on the synthesized double-stranded DNA and measured.

This step is initiated in the presence of at least a RNA polymerase, ribonucleoside triphosphates and a fluorescent intercalative dye-labeled probe complimentary to the resulting. Therefore, the RNA producing and measuring step can be initiated only by adding these reagents after the DNA producing step. The probe hybridizes with the resulting the RNA to alter the fluorescence of the fluorescent intercalative dye as the label of the probe. Therefore, it is possible to detect the specific nucleic acid in the sample and determine its initial amount by measuring the fluorescence intensity of the reaction mixture. The RNA polymerase used in the RNA producing and measuring step is not particularly limited, and for example, those commercially available such as T7 RNA polymerase, T3 polymerase and SP6 RNA polymerase may be used.

The probe used in the present invention is an oligonucleotide which hybridizes selectively with the RNA synthesized by the action of the RNA polymerase and is labeled with a fluorescent intercalative dye which alters the fluorescence on binding to double-stranded DNA (Japanese Patent Application JP7-185599, EP-A-714986, Nucleic Acid Research, 24(24), 4992–4997(1996)). The fluorescent intercalative dye is not particularly limited, as long as it alters the fluorescence on binding to double-stranded DNA. However, those which enhance the fluorescence on intercalation are preferable in view of the easiness of monitoring, and particularly, thiazole orange, oxazole yellow and their derivatives are preferable because they shows radical alternation in the fluorescence.

The fluorescent intercalative dye is linked to the oligonucleotide by a covalent bond, if necessary, via a linker of an appropriate length. Although any linkers that do not hinder the fluorescent intercalative dye from binding to double-stranded DNA may be used, difunctional hydrocarbons having functional groups at both ends are preferred because they are easy to link to oligonucleotides. Further, for example, a commercial kit (C6-Thiolmodifier, Clontech) may be used. The fluorescent intercalative dye as the label may be linked to any sites of the nucleotide, including the 5'-end, the 3'-end and the center, as long as the linkage neither hinders the fluorescent intercalative dye from intercalating to double-stranded DNA nor hinders the oligonucleotide from hybridizing with the RNA. The region of the probe which is complimentary to the RNA is preferably from 6 to 100 nucleotides, more preferably from 10 to 30 nucleotides long in order to secure the specificity for the RNA. As described above, because the RNA polymerase is brought into action in the presence of a fluorescent intercalative dye-labeled probe so that the probe hybridizes with the transcription product RNA, the method of the present invention makes it possible to precisely detect and quantify a target nucleic acid in samples by monitoring the fluorescence intensity of the reaction mixture without denaturing and annealing procedures for hybridization. Namely, fluorescent intercalative dye as the label of the probe alters the fluorescence on hybridization of the probe with the RNA produced depending on the initial amount of a specific nucleic acid in the sample, it is possible to detect and quantify the hybrid without separation of the unhybridized excessive probe, and to provide a simple method of homogeneous one-step assay of a nucleic acid having a specific sequence.

The DNA producing step of the present invention may utilize PCR. In such a case, the double-stranded DNA sequence having a promoter sequence for RNA polymerase upstream and a specific nucleic acid sequence downstream is amplified to a large amount in the DNA producing step and then subjected to the RNA producing and measuring step. For the amplification by PCR, the ordinary PCR process for denaturing and annealing comprising heating and cooling is conducted by using the above-mentioned two primers in the DNA producing step.

The present invention is described in more detail by reference to Examples. However, the present invention is by no means restricted to these specific Examples.

Figure 1:
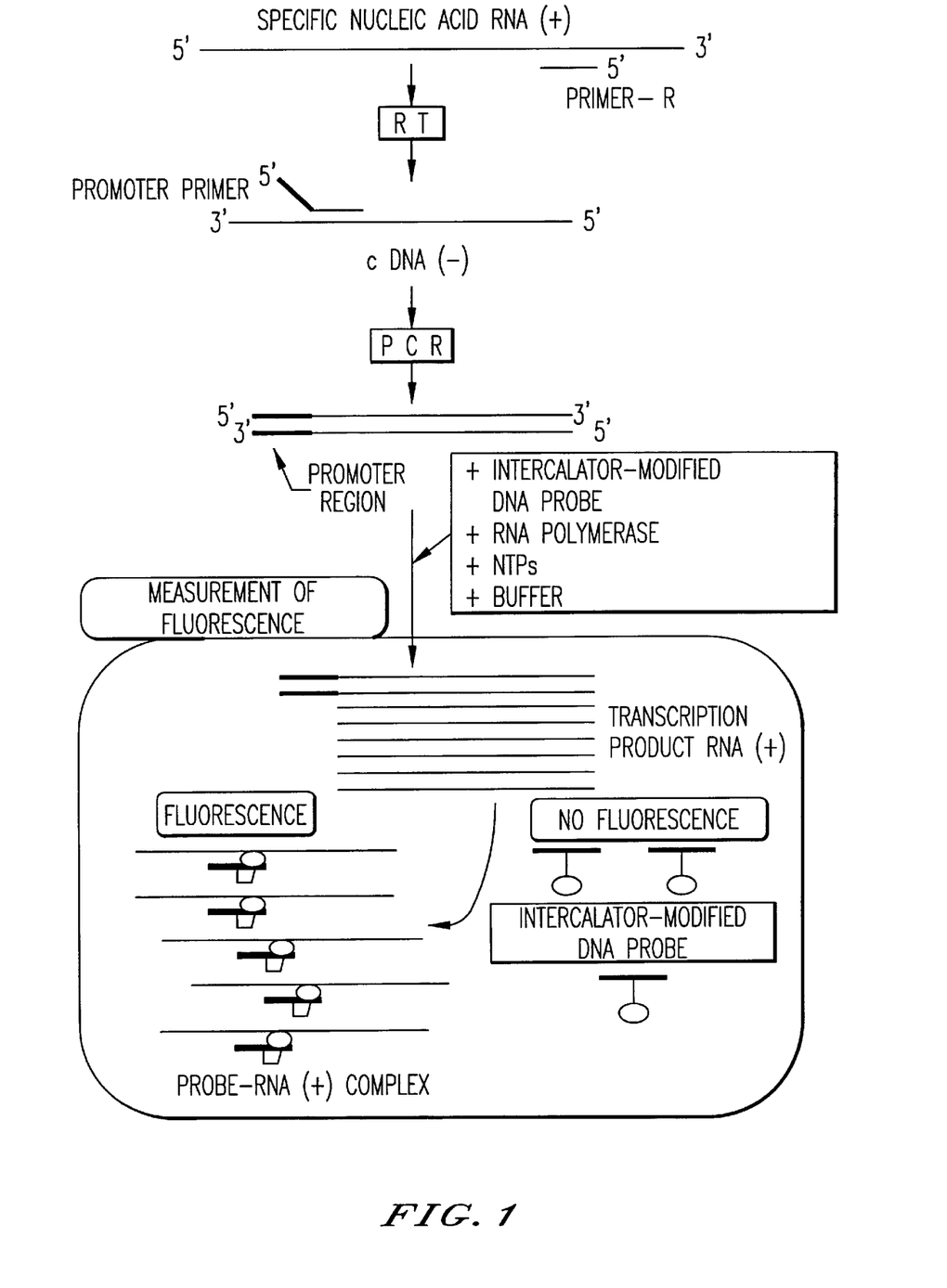
FIG. 1 illustrates one embodiment of the present invention wherein the target nucleic acid in the sample is single-stranded RNA.

FIG. 1 illustrates an embodiment of the present invention wherein the specific nucleic acid in the sample is a single-stranded RNA. In the DNA producing step, a reverse transcriptase synthesizes the cDNA of the specific nucleic acid in the presence of a primer for reverse transcription and deoxyribonucleoside triphosphates. The synthesized cDNA is complimentary to the specific nucleic acid sequence.

Then, PCR is conducted by adding a promoter primer having the same sequence as the 5'-end of the specific nucleic acid and a thermoresistant DNA polymerase to give a double-stranded DNA having a promoter region for an RNA polymerase at the 5'-end.

Then, the RNA producing and measuring step follows. A reagent containing a fluorescent intercalative dye-labeled probe, an RNA polymerase and ribonucleoside triphosphates is added to the reaction solution, and then the reaction solution is incubated at the optimum temperature for the RNA polymerase. The RNA polymerase transcribes the double-stranded DNA having a promoter region produced in the DNA producing step into an RNA having the specific nucleic acid sequence. The RNA produced by the transcription hybridizes with the fluorescent intercalative dye-labeled probe coexisting in the reaction solution to enhance the fluorescence intensity in proportion to the amount of the hybrid. Therefore, it is possible to detect the specific nucleic acid or determine the initial amount of the specific nucleic acid by measuring the fluorescence intensity of the reaction solution before and after, or during this step.

When the specific nucleic acid in the sample is double-stranded DNA, PCR in the presence of a pair of the primer and a promoter primer, deoxyribonucleoside triphosphates and thermoresistant DNA polymerase to produce a double-stranded DNA having a promoter region for an RNA polymerase is followed by the above-mentioned procedures.

EXAMPLE 1

The method of the present invention was applied to assay of a recombinant HCV RNA, and its lower limit of detection was evaluated.

(1) A recombinant HCV RNA (containing the bases Nos. 1 to 1863 of Kato et al.: Kato, N., Hijikata, M., Ootsuyama, Y., et al. (1990) Proc. Natl. Acad. Sci. USA, 87, 9524–9528) was diluted to 50, 10, 5, 0 copy/10 µl with an RNA diluent of the following composition to prepare samples.

Composition of RNA diluent
   10 mM Tris-HCl (pH 8.0)
   0.1 mM EDTA
   100 μg/ml yeast RNA
(2) A volume of 5 μl of a reaction solution of the following composition was dispensed into PCR tubes each, and 10 μl of the samples were added thereto.
Composition of reaction solution
   30 mM Tris-HCl (pH 8.3)
   150 mM KCl
   13.6 mM MgCl2
   4.3 mM NTPs
   3 mM DTT
   3 U/μl RNase inhibitor
   6 U/μl MMLV reverse transcriptase
   3.6 μM Primer;
      5'-ACTCGCAAGCACCCTATC-3' SEQ ID NO: 1
(3) Reverse transcription was conducted in a thermal cycler.
Conditions for reverse transcription
   42° C. for 10 minutes
   99° C. for 6 minutes
(4) 60 μl of a PCR solution of the following composition was added.
Composition of the PCR solution
   10 mM Tris-HCl (pH 8.3)
   50 mM KCl
   1.6 mM MgCl2
   0.025% Nonidet P-40
   37.5 U/ml Taq DNA polymerase for hot start
   0.3 μM Promoter primer;
      5'-ATTTAGGTGACACTATAGAATACAACA CTCCACCATAGATCACTC-3' SEQ ID NO: 2
(5) PCR was conducted in a thermal cycler under the following conditions.
Conditions for PCR
   (a) 95° C. for 9 minutes After (a), a cycle of the following (b) to (d) was repeated 40 times.
   (b) 95° C. for 30 seconds
   (c) 65° C. for 30 seconds
   (d) 72° C. for 1 minute
(6) 70 μl of each of the resulting PCR mixtures was mixed with 65.3 μl of a transcription solution of the following composition and then transferred into a quartz cuvette maintained at 37° C. in a fluorescence spectrometer.
Composition of the transcription solution
   75.3 mM Tris-HCl (pH 8.0)
   15.1 mM MgCl2
   10.7 mM DTT
   0.86 mM NTPs
   4.3 mM Spermidine
   2.2 U/μl RNase Inhibitor
   53.6 nM YO-271 (fluorescent intercalative dye-labeled probe);
      5'-CTCGC*GGGGGCTG-3' SEQ ID NO: 3
(* indicates the site labeled with the fluorescent intercalative dye)
(7) Then, to the reaction mixtures, 4.7 μl of SP6 RNA polymerase (30 U/μl) was added to make the total amount 140 μl, the fluorescence intensity was monitored at 37° C. for 30 minutes (excitation wavelength 490 nm, emission wavelength 510 nm).
(8) The average and the standard deviation of the increase in the fluorescence intensity for 0 copy samples were calculated, and the cutoff for the presence of the target RNA was set at (average)+3×(standard deviation).

Figure 2:
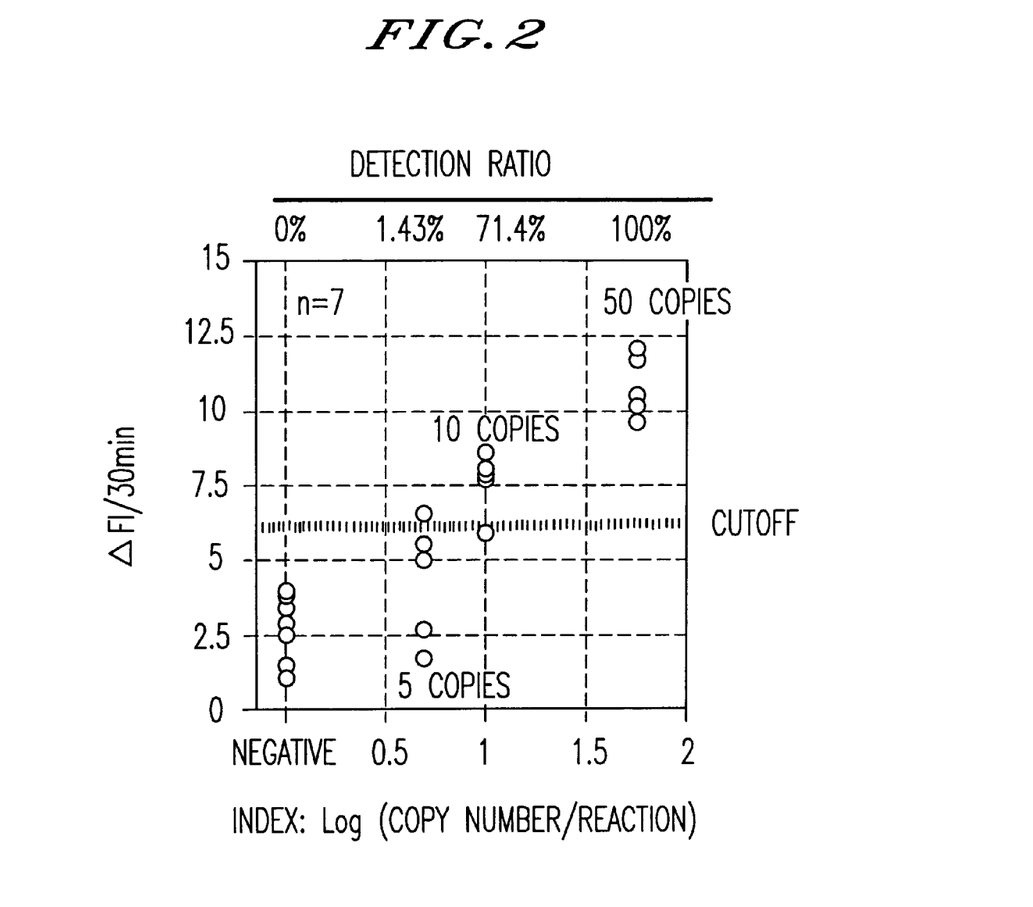
FIG. 2 shows the initial copy numbers of a recombinant HCV RNA and the fluorescence intensities measured the method of the present invention. The ordinate indicates the increase in fluorescence intensity during 30 minutes of in vitro transcription.

FIG. 2 shows the increases in fluorescence during 30 minutes and the detection ratio. The increase in fluorescence intensity for 10 copies was significantly distinguished from that for 0 copy (t test, significance level 1%) and 10 copies of the recombinant HCV RNA were detectable.

Figure 3:
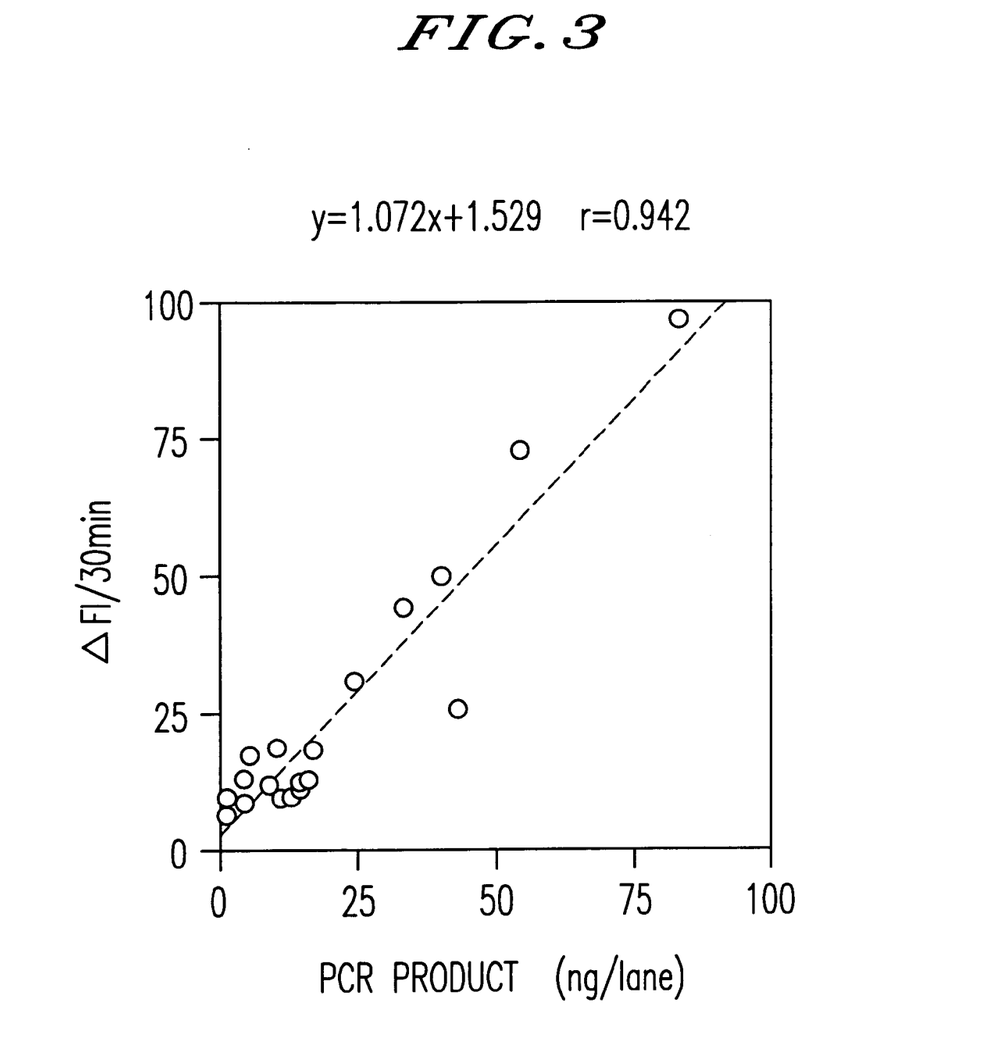
FIG. 3 shows the amounts of the PCR product from the target nucleic acid and the fluorescence intensities measured by assaying a recombinant HCV RNA by the method of the present invention.

FIG. 3 shows the correlation between the amounts of DNA calculated from the densities of the ethidium bromide-stained bands obtained by agalose electrophoresis of portions of the reaction mixtures immediately after the addition of SP6 RNA polymerase and the increases in fluorescence intensity. A good correlation was found between the amounts of the PCR products and the increases in fluorescence intensity. These results confirmed that the present invention allows sensitive sequence-specific assay of specific nucleic acids in samples.

EXAMPLE 2

Serum samples from 20 patients with chronic hepatitis C were assayed by the method of the present invention, and the results were compared with those obtained by using a commercial HCV RNA detection kit (Amplicore HCV, Japan Rosh).

(1) Nucleic acid was extracted from 120 μl of each of the serum samples from 20 patients with chronic hepatitis C by using a organic solvent and a protein modifier.

(2) The pellets of the extracted nucleotide were dissolved in 72 μl of the diluent of the kit, and 50 μl portions of the resulting solutions were used for the assay by the commercial kit. The assay was performed in accordance with the manufacture's instructions.

(3) In the method of the present invention, the pellets of the extracted nucleic acid were dissolved in 14 μl of a diluent of the following composition, and 10 μl portions of the resulting solutions were used for the assay. The assay was conducted in the same manner as in Example 1.

Composition of diluent for samples
   10 mM Tris-HCl (pH 8.0)
   0.1 mM EDTA
   100 μg/ml yeast RNA
   1 mM DTT
   2 U/μl RNase Inhibitor (4) For the samples found negative (−/−) by the commercial kit, the increase in fluorescence intensity during a reaction time of 30 minutes and the standard deviation were calculated. The cutoff for the method of the present invention was set at (the average increase in fluorescence intensity)+3×(the standard deviation).

The correlation between the results obtained by the method of the present invention and by the commercial kit is shown in the Table given below. For the samples found negative (−/−) and positive (+/+) according to the commercial kit, the results obtained by using the commercial kit were compared with those obtained by the method according to the present invention. The results obtained by these two methods agreed at a probability of 81.3% ({(4+9)/(7+9)}× 100=13/16×100=81.3).

TABLE 1

| | | Method of the present invention | | | |
|---|---|---|---|---|---|
| | | +/+ | +/- | -/- | Total |
| Amplicore results | +/+ | 4 | 0 | 3 | 7 |
| | +/- | 0 | 1 | 3 | 4 |
| | -/- | 0 | 0 | 9 | 9 |
| Total | | 4 | 1 | 15 | 20 |

From these results, it was confirmed that the method of the present invention facilitates detection of specific nucleic acids in clinical samples as compared with the conventional method.

EXAMPLE 3

The method of the present invention was applied to assay of a recombinant HCV RNA, and its lower limit of detection was evaluated.

(1) A recombinant HCV RNA (containing the bases Nos. 1 to 1863 of Kato et al.) was diluted to 50, 10, 5, 1, 0 copy/10 $\mu$l with the same RNA diluent as in Example 1.

(2) A volume of 5 $\mu$l of a reaction solution of the following composition was dispensed into PCR tubes each, and 10 $\mu$l of the samples were added thereto.

Composition of reaction solution
30 mM Tris-HCl (pH 8.3)
150 mM KCl
13.6 mM MgCl2
4.3 mM dNTPs
3 mM DTT
3 U/$\mu$l RNase Inhibitor
6 U/$\mu$l MMLV reverse transcriptase
3.6 $\mu$M Primer;
5'-GCACTCGCAAGCACCCTATCA-3' SEQ ID NO: 4

(3) Reverse transcription was conducted in a thermal cycler under the following conditions.

Conditions for reverse transcription
42° C. for 10 minutes
99° C. for 6 minutes (4) 60 $\mu$l of a PCR solution of the following composition was added.

Composition of the PCR solution
10 mM Tris-HCl (pH 8.3)
50 mM KCl
1.6 mM MgCl2
0.025% Nonidet P-40
37.5 U/ml Taq DNA polymerase for hot start
0.3 $\mu$l Promoter primer;
5'-ATTTAGGTGACACTATAGAATACAACACTCCACCATAGATCACTCCCCTG-3' SEQ ID NO: 5

(5) PCR was conducted in a thermal cycler under the following conditions.

Conditions for PCR
(a) 95° C. for 9 minutes After (a), a cycle of the following (b) to (d) was repeated 40 times.
(b) 95° C. for 30 seconds
(c) 67° C. for 30 seconds
(d) 72° C. for 1 minute (6) 70 $\mu$l of each of the resulting PCR mixtures was mixed with 65.3 $\mu$l of the same transcription solution as in Example 1 and then transferred into a quartz cuvette maintained at 37° C. in a fluorescence spectrometer.

(7) Then, to the reaction mixtures, 4.7 $\mu$l of SP6 RNA polymerase (30 U/$\mu$l) was added to make the total amount 140 $\mu$l, the fluorescence intensity was monitored at 37° C. for 30 minutes (excitation wavelength 490 nm, emission wavelength 510 nm).

(8) The average and the standard deviation of the increase in the fluorescence intensity for 0 copy samples were calculated, and the cutoff for the presence of the target RNA was set at (average)+3×(standard deviation).

Figure 4:
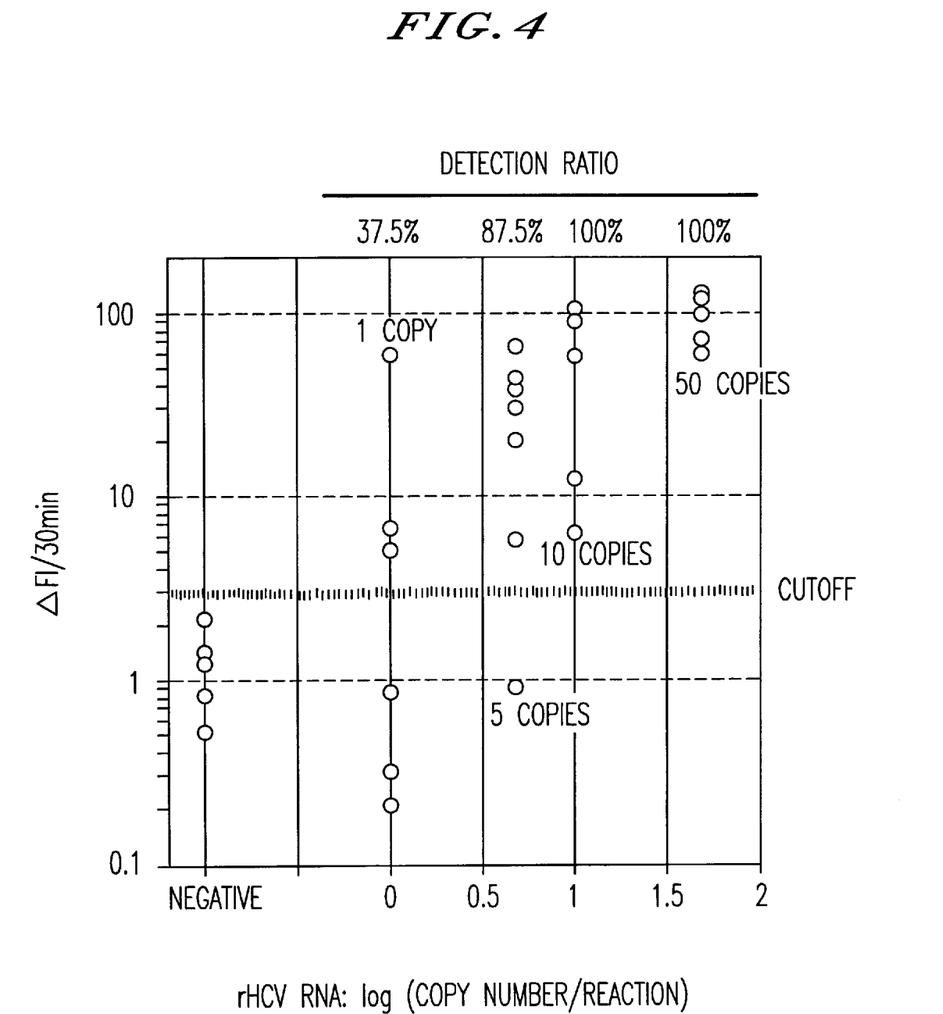
FIG. 4 shows the initial copy numbers of a recombinant HCV RNA and the fluorescence intensities measured the method of the present invention.

FIG. 4 shows the increases in fluorescence intensity and the detection ratios. All the samples containing at least 10 copies of the recombinant HCV RNA were judged positive. 87.5% of the samples containing 5 copies were judged positive. These facts confirmed that the present invention allows sensitive sequence-specific detection of specific nucleic acids.

As is evident from the above description, the present invention allows detection and quantification of specific nucleic acids anticipated in samples by simple homogeneous assay without using supports and separating the unhybridized excessive probe in the RNA producing and measuring step which involves monitoring of the fluorescent intensity. Further, because the present invention removes the necessity of denaturing and annealing in the step and only requires addition of the necessary reagent to sample solutions and monitoring of fluorescence intensity at a constant temperature in the step, the step can be performed only by one operation, namely, bringing the reagent into contact.

Namely, according to the present invention, because the fluorescent intercalative dye as the label of the probe alters the fluorescence, for example enhances the fluorescence intensity, on hybridization of the probe with the RNA (which contains the same base sequence as the specific nucleic acid sequence) produced in the RNA producing and measuring step, it is possible to detect and quantify the resulting hybrid without separating the unhybridized excessive probe. Therefore, use of vessels made of a material optically transparent at the excitation and emission wavelength of the fluorescent intercalative dye to be used allows continuous assay while removing the problem of the chance of false positive results due to carryover of the amplification product because there is no need to collect reaction solutions from vessels.

Further, according to the present invention, since the probe specifically recognizes a specific nucleic acid sequence and alters the fluorescence on hybridization, if PCR is performed in the DNA producing step, the probe does not hybridize with a primer dimer produced as a by-product, and therefore, the primer dimer does not contribute to the change in the fluorescence of the reaction solution. Accordingly, sequence-specific assay of a specific nucleic acid can be achieved without separation of the primer dimer after PCR by monitoring the fluorescence of the reaction solution. In addition, since the RNA producing and measuring step is initiated by adding an RNA polymerase, ribonucleoside triphosphates and the probe DNA solutions obtained in the DNA producing step, the present invention obviates cumbersome operations such as transferring a reaction solution from one vessel to another and provides a quite simple assay method useful for clinical diagnosis.

What is claimed is:

1. A method for detecting a target nucleic acid, comprising:

(a) adding to a sample an oligonucleotide primer, wherein the nucleotide sequence of the oligonucleotide primer is complementary to the target nucleic acid sequence and comprises a RNA polymerase promoter sequence, wherein a duplex is formed between the target nucleic acid and the primer when the target sequence is present in the sample;

(b) elongating the primer in a duplex with the target nucleic acid sequence in (a) to produce a double stranded polynucleotide;

(c) reacting the double stranded polynucleotide produced in (b) with RNA polymerase to produce RNA;

(d) adding a oligonucleotide probe complementary to the RNA in (c), wherein the probe is labeled with a fluorescent intercalative dye;

(e) measuring the fluorescence of the intercalative dye.

2. The method of claim 1, wherein (d) is subsequent to (c).

3. The method of claim 1, wherein (d) is essentially at the same time as (c).

4. The method of claim 1, wherein the fluorescence properties of the probe labeled with a fluorescent intercalative dye in (d) changes upon hybridization with the RNA.

5. The method of claim 1, wherein the intercalative dye is thiazole orange.

6. The method of claim 1, wherein the intercalative dye is oxazole yellow.

7. The method of claim 1, wherein the RNA polymerase is T3 polymerase.

8. The method of claim 1, wherein the RNA polymerase is T7 polymerase.

9. The method of claim 1, wherein the RNA polymerase is SP6 polymerase.

10. The method of claim 1, wherein (b) comprises a polymerase chain reaction.

11. A method for detecting a target single-stranded RNA, comprising:
   (a) adding to a sample an oligonucleotide primer complementary to the target single-stranded RNA sequence wherein a duplex is formed between the target nucleic acid and the primer when the target is present in a sample;
   (b) elongating the primer in (a) to produce a cDNA molecule;
   (c) adding to the cDNA produced in (b) a oligonucleotide primer complementary to the target nucleic acid sequence and further consisting of a RNA polymerase promoter sequence wherein a duplex is formed between the target nucleic acid sequence and the primer;
   (d) elongating the primer in (c) to produce a double stranded polynucleotide;
   (e) reacting the double stranded polynucleotide produce in (d) with RNA polymerase;
   (f) adding a oligonucleotide probe complementary to the RNA of (e), wherein the probe is labeled with a fluorescent intercalative dye;
   (g) measuring the fluorescence of the intercalative dye.

12. The method of claim 11, wherein (f) is subsequent to (e).

13. The method of claim 11, wherein (f) is essentially at the same time as (e).

14. The method of claim 11, wherein the fluorescence properties of the probe labeled with a fluorescent intercalative dye in (f) changes upon hybridization with the RNA.

15. The method of claim 11, wherein the intercalative dye is thiazole orange.

16. The method of claim 11, wherein the intercalative dye is oxazole yellow.

17. The method of claim 11, wherein the elongating in (b) is reverse transcription.

18. The method of claim 11, wherein the RNA polymerase is T3 polymerase.

19. The method of claim 11, wherein the RNA polymerase is T7 polymerase.

20. The method of claim 11, wherein the RNA polymerase is SP6 polymerase.

21. The method of claim 11, wherein the elongating in (d) is the polymerase chain reaction.

* * * * *